US011793408B2

United States Patent
Ansari et al.

(10) Patent No.: US 11,793,408 B2
(45) Date of Patent: Oct. 24, 2023

(54) METHOD AND SYSTEM FOR PREDICTING LOCATION AND DEPTH OF ABNORMAL TISSUE IN BREAST OF SUBJECT

(71) Applicants: THE SECRETARY, MINISTRY OF ELECTRONICS AND INFORMATION TECHNOLOGY, GOVT. OF INDIA, New Delhi (IN); THE DIRECTOR GENERAL, CENTRE FOR MATERIALS FOR ELECTRONICS TECHNOLOGY (C-MET), Maharashtra (IN); THE PRINCIPAL, GOVERNMENT ENGINEERING COLLEGE, Kerala (IN); THE DIRECTOR, MALABAR CANCER CENTRE (MCC), Kerala (IN)

(72) Inventors: Seema Ansari, Kerala (IN); Muralidharan Malamal Neelanchery, Kerala (IN); Arathy Kottapurath, Kerala (IN); Eva Ignatious, Kerala (IN); Ranjith Kizhupadath Ravindran, Kerala (IN); Deepak Puthan Purayil, Kerala (IN); Sudheesh Raveendran Nair Sarojini, Kerala (IN); Satheesan Balasubramanian, Kerala (IN)

(73) Assignees: THE SECRETARY, MINISTRY OF ELECTRONICS AND INFORMATION TECHNOLOGY, GOVT. OF INDIA, New Delhi (IN); THE DIRECTOR GENERAL, CENTRE FOR MATERIALS FOR ELECTRONICS TECHNOLOGY (C-MET), Maharashtra (IN); THE PRINCIPAL, GOVERNMENT ENGINEERING COLLEGE, Kerala (IN); THE DIRECTOR, MALABAR CANCER CENTRE (MCC), Kerala (IN)

(*) Notice: Subject to any disclaimer, the term of this patent is extended or adjusted under 35 U.S.C. 154(b) by 0 days.

(21) Appl. No.: 17/851,810

(22) Filed: Jun. 28, 2022

(65) Prior Publication Data
US 2022/0354369 A1 Nov. 10, 2022

Related U.S. Application Data

(62) Division of application No. 15/926,935, filed on Mar. 20, 2018, now Pat. No. 11,375,901.

(30) Foreign Application Priority Data

Dec. 28, 2017 (IN) .............................. 201711047118

(51) Int. Cl.
*A61B 5/00* (2006.01)
*A61B 5/01* (2006.01)
(Continued)

(52) U.S. Cl.
CPC ............ *A61B 5/0091* (2013.01); *A61B 5/015* (2013.01); *A61B 5/4312* (2013.01);
(Continued)

(58) Field of Classification Search
CPC ..... A61B 5/0091; A61B 5/015; A61B 5/4312; A61B 5/7275; A61B 5/06; G06T 7/0012
See application file for complete search history.

(56) References Cited

U.S. PATENT DOCUMENTS

2009/0048523 A1 2/2009 Schlagheck et al.
2010/0298895 A1* 11/2010 Ghaffari ............. A61B 5/14546
607/116
(Continued)

OTHER PUBLICATIONS

Saniei et al., Parameter estimation of breast tumour using dynamic neural network from thermal pattern, Journal of Advanced Research (2016) 7, 1045-1055 (Year: 2016).*
(Continued)

*Primary Examiner* — John Denny Li
(74) *Attorney, Agent, or Firm* — Foley & Lardner LLP

(57) ABSTRACT

The present disclosure relates to method for predicting location and depth of abnormal tissue in breast tissue by
(Continued)

prediction system. The prediction system predicts location based on 2D thermal image generated based on temperature values and intermediate temperature values. The intermediate temperature values are estimated using triangular and rectangular patterns formed on pre-defined model of breast, thermal conductivity of breast tissue, 2D coordinates on one of triangular and rectangular patterns and temperature values at steady state of breast tissue. The depth is predicted based on 3D thermal image of breast tissue generated using temperature values and intermediate temperature values and error parameter. The intermediate temperature values are estimated based on one of tetrahedral and hexahedral patterns formed on predefined model of breast, density value, thermal conductivity of tissue, blood perfusion rate, specific heat capacity of blood, 3D coordinates, arterial temperature and metabolic heat generation value in normal and abnormal tissue.

21 Claims, 6 Drawing Sheets

(51) Int. Cl.
*G06T 7/00* (2017.01)
*G16H 50/30* (2018.01)
*A61B 5/06* (2006.01)

(52) U.S. Cl.
CPC .......... *A61B 5/7275* (2013.01); *G06T 7/0012* (2013.01); *G16H 50/30* (2018.01); *A61B 5/06* (2013.01)

(56) References Cited

U.S. PATENT DOCUMENTS

| | | |
|---|---|---|
| 2013/0035921 A1 | 2/2013 | Rodriguez-Ponce et al. |
| 2014/0112561 A1 | 4/2014 | Arnon et al. |
| 2020/0069191 A1* | 3/2020 | Cantú ................. A61B 5/6804 |
| 2021/0251492 A1* | 8/2021 | Toledano ............ A61B 5/0088 |

OTHER PUBLICATIONS

Saniei et al., "Parameter estimation of breast tumour using dynamic neural network from thermal pattern," Journal of Advanced Research, vol. 7, 2016, pp. 1045-1055.

* cited by examiner

METHOD AND SYSTEM FOR PREDICTING LOCATION AND DEPTH OF ABNORMAL TISSUE IN BREAST OF SUBJECT

CROSS-REFERENCE TO RELATED APPLICATION

The present application is a Divisional of U.S. patent application Ser. No. 15/926,935, filed on Mar. 20, 2018, which claims priority to and the benefit of Indian Patent Application No. 201711047118, filed on Dec. 28, 2017. The contents of these applications are hereby incorporated by reference in their entireties.

TECHNICAL FIELD

The present subject matter is related in general to a prediction system, more particularly, but not exclusively to, method and system for predicting location and depth of abnormal tissue in a breast tissue of a subject.

BACKGROUND

Today, breast cancer is the most common invasive cancer in women worldwide. It accounts for 16% of all female cancers and 22.9% of invasive cancers in women. Hence, efforts to find a technique for early detection of breast cancer is a very active field of research all over the world. Till today, mammography has been approved as the golden standard for the screening of breast cancer. However, for younger women (age<40 years) having dense breast, detection of breast cancer using mammogram is difficult. It involves X-ray exposure and no privacy is ensured. Moreover, at least 10% of breast cancers cannot be identified by mammography, even when they are palpable.

Studies have proved that a cancerous cell, compared to that of a normal cell, will have higher temperature. The temperature rise in cancerous cell is due to the increased blood flow and higher or uncontrolled metabolic activities of cancerous cells. Cancerous tissues do not have an intact sympathetic nervous system and hence cannot regulate heat loss. When breast tissue is cooled, blood vessels of normal tissue respond by constricting to conserve heat, while tumor tissue remains hot. Detecting this temperature difference with high accuracy helps early detection of breast cancer. Tumor emit more heat than their surrounding tissues and it is measurable with sensitive and accurate thermal sensors. Therefore, thermography, as an alternate method, is gaining increased importance.

Existing technology discloses various methods for detection of abnormal cells in the breast tissue. Depth, size and location of cancerous tissue will aide in further diagnosis and treatment of cancer. However, the existing methods do not disclose exact location where the abnormality is present, and depth associated with the abnormal tissue.

The information disclosed in this background of the disclosure section is only for enhancement of understanding of the general background of the invention and should not be taken as an acknowledgement or any form of suggestion that this information forms the prior art already known to a person skilled in the art.

SUMMARY

In an embodiment, the present disclosure relates to a method for predicting location of abnormal tissue in a breast tissue of a subject, the method comprising receiving a plurality of temperature values associated with a breast of a subject from a device. The device comprises a plurality of thermal sensors locatable on pre-determined positions of the breast of the subject. The method comprises estimating a plurality of intermediate temperature values, within the plurality of temperature values, based on at least one of triangular patterns and rectangular patterns formed on a pre-defined model of the breast of the subject, thermal conductivity of the breast tissue, two-dimensional coordinates on at least one of the triangular patterns and the rectangular patterns and temperature values at steady state of the breast tissue of the subject, generating a two-dimensional thermal image of the breast of the subject, based on the plurality of the temperature values and the plurality of intermediate temperature values and predicting a location of abnormal tissue in the breast tissue of the subject, based on the two-dimensional thermal image, wherein the location of the abnormal tissue is predicted by the two-dimensional coordinates associated with an abnormal temperature value, among the plurality of temperature values and the plurality of intermediate temperature values.

In an embodiment, the present disclosure relates to a prediction system for predicting location of abnormal tissue in a breast tissue of a subject. The prediction system comprises a processor and a memory communicatively coupled to the processor, wherein the memory stores processor executable instructions, which, on execution, may cause the prediction system to receive a plurality of temperature values associated with a breast of a subject from a device. The device comprises a plurality of thermal sensors locatable on pre-determined positions of the breast of the subject. The prediction system estimates a plurality of intermediate temperature values, within the plurality of temperature values, based on at least one of triangular patterns and rectangular patterns formed on a pre-defined model of the breast of the subject, thermal conductivity of the breast tissue, two-dimensional coordinates on at least one of the triangular patterns and the rectangular patterns and temperature values at steady state of the breast tissue of the subject, generates a two-dimensional thermal image of the breast of the subject, based on the plurality of the temperature values and the plurality of intermediate temperature values and predicts a location of abnormal tissue in the breast tissue of the subject, based on the two-dimensional thermal image. The location of the abnormal tissue is predicted by the two-dimensional coordinates associated with an abnormal temperature value, among the plurality of temperature values and the plurality of intermediate temperature values.

In an embodiment, the present disclosure relates to a non-transitory computer readable medium including instructions stored thereon that when processed by at least one processor may cause a prediction system to receive a plurality of temperature values associated with a breast of a subject from a device. The device comprises a plurality of thermal sensors locatable on pre-determined positions of the breast of the subject. The instruction causes the processor to estimate a plurality of intermediate temperature values, within the plurality of temperature values, based on at least one of triangular patterns and rectangular patterns formed on a pre-defined model of the breast of the subject, thermal conductivity of the breast tissue, two-dimensional coordinates on at least one of the triangular patterns and the rectangular patterns and temperature values at steady state of the breast tissue of the subject, generate a two-dimensional thermal image of the breast of the subject, based on the plurality of the temperature values and the plurality of intermediate temperature values and predict a location of abnormal tissue in the breast tissue of the subject, based on the two-dimensional thermal image. The location of the abnormal tissue is predicted by the two-dimensional coordinates associated with an abnormal temperature value, among the plurality of temperature values and the plurality of intermediate temperature values.

In another embodiment, the present disclosure relates to a method for predicting depth of abnormal tissue in a breast tissue of a subject, the method comprising receiving a plurality of temperature values associated with a breast of a subject from a device. The device comprises a plurality of thermal sensors locatable on pre-determined positions of the breast of the subject. The method comprises estimating a plurality of intermediate temperature values within the plurality of temperature values, based on at least one of tetrahedral patterns and hexahedral patterns formed on a predefined model of the breast of the subject, density value, thermal conductivity of the tissue, blood perfusion rate, specific heat capacity of the blood, three-dimensional coordinates on at least one of the tetrahedral patterns and the hexahedral patterns, arterial temperature and metabolic heat generation value in a normal and in an abnormal tissue, generating a three-dimensional thermal image of the breast of the subject based on the plurality of temperature values and the plurality of intermediate temperature values and an error parameter and predicting depth of the abnormal tissue in the breast tissue of the subject based on, the three-dimensional thermal image. The depth of the abnormal tissue is predicted by the three-dimensional coordinates of a temperature value associated with a higher temperature value among the plurality of temperature values and the plurality of intermediate temperature values.

In an embodiment, the present disclosure relates to a prediction system for predicting depth of abnormal tissue in a breast tissue of a subject. The prediction system comprises a processor and a memory communicatively coupled to the processor, wherein the memory stores processor executable instructions, which, on execution, may cause the prediction system to receive a plurality of temperature values associated with a breast of a subject from a device. The device comprises a plurality of thermal sensors locatable on pre-determined positions of the breast of the subject. The prediction system estimates a plurality of intermediate temperature values within the plurality of temperature values, based on at least one of tetrahedral patterns and hexahedral patterns formed on a predefined model of the breast of the subject, density value, thermal conductivity of the tissue, blood perfusion rate, specific heat capacity of the blood, three-dimensional coordinates on at least one of the tetrahedral patterns and the hexahedral patterns, arterial temperature and metabolic heat generation value in a normal and in an abnormal tissue, generates a three-dimensional thermal image of the breast of the subject based on the plurality of temperature values and the plurality of intermediate temperature values and an error parameter and predicts depth of the abnormal tissue in the breast tissue of the subject based on, the three-dimensional thermal image. The depth of the abnormal tissue is predicted by the three-dimensional coordinates of a temperature value associated with a higher temperature value among the plurality of temperature values and the plurality of intermediate temperature values.

In an embodiment, the present disclosure relates to a non-transitory computer readable medium including instructions stored thereon that when processed by at least one processor may cause a prediction system to receive a plurality of temperature values associated with a breast of a subject from a device. The device comprises a plurality of thermal sensors locatable on pre-determined positions of the breast of the subject. The instruction causes the processor to estimate a plurality of intermediate temperature values within the plurality of temperature values, based on at least one of tetrahedral patterns and hexahedral patterns formed on a predefined model of the breast of the subject, density value, thermal conductivity of the tissue, blood perfusion rate, specific heat capacity of the blood, three-dimensional coordinates on at least one of the tetrahedral patterns and the hexahedral patterns, arterial temperature and metabolic heat generation value in a normal and in an abnormal tissue, generate a three-dimensional thermal image of the breast of the subject based on the plurality of temperature values and the plurality of intermediate temperature values and an error parameter and predict depth of the abnormal tissue in the breast tissue of the subject based on, the three-dimensional thermal image. The depth of the abnormal tissue is predicted by the three-dimensional coordinates of a temperature value associated with a higher temperature value among the plurality of temperature values and the plurality of intermediate temperature values.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

Figure 1:
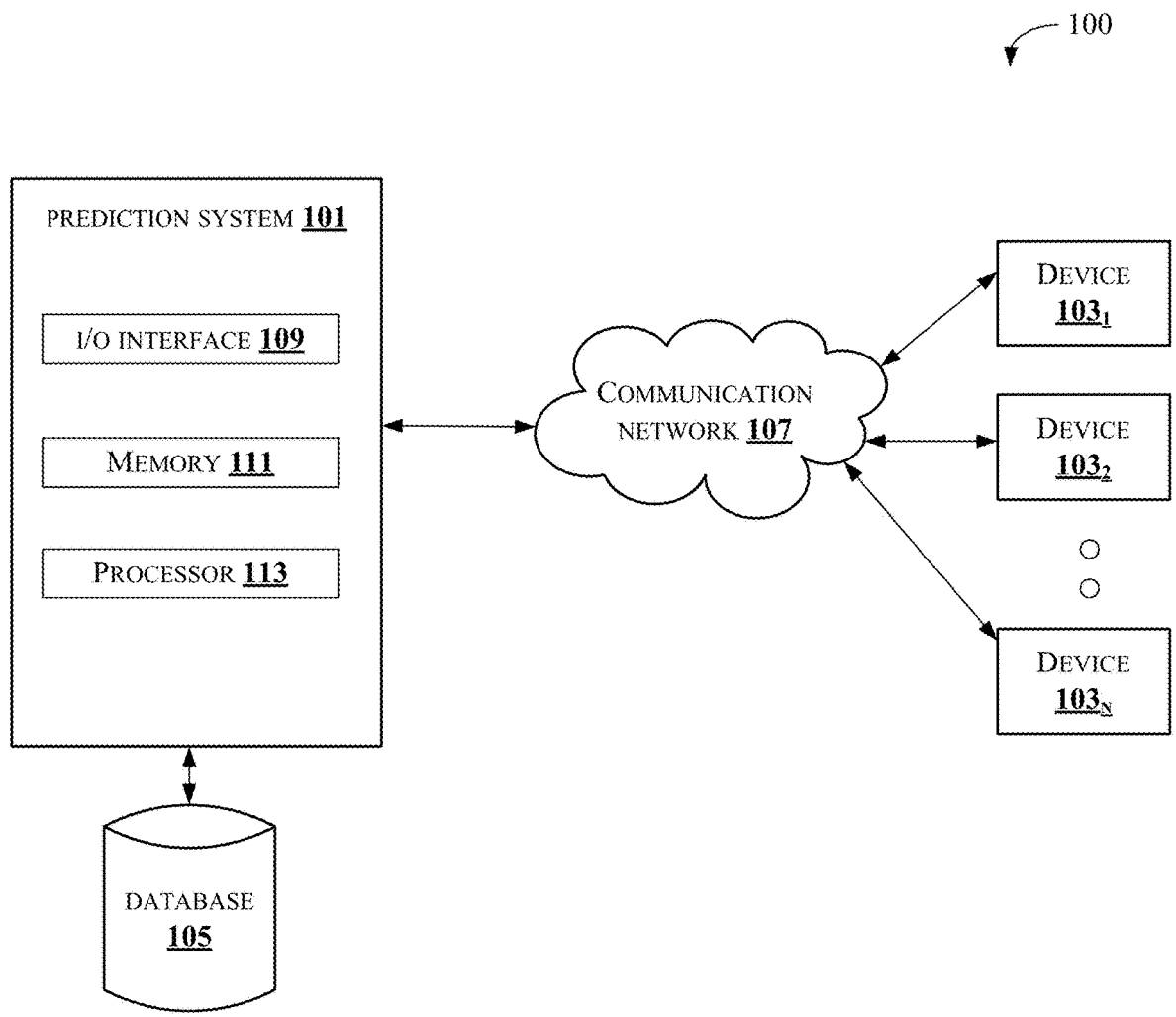
FIG. 1 illustrates an exemplary environment for predicting location and depth of an abnormal tissue in a breast tissue of a subject in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

The present disclosure relates to a method and a prediction system for predicting location and depth of an abnormal tissue in a breast tissue of a subject. In an embodiment, the prediction system may predict the exact location where the abnormal tissue is located and the depth of the abnormal tissue in the breast tissue. To check abnormalities in the breast tissue, the subject may initially wear a device which is specifically developed using thermal sensors. Particularly, the device may be a thermography device, which may be made of calibrated interchangeable thermal sensors placed on the device. In an embodiment, the thermal sensors are placed at pre-determined positions on the device. To predict the location and depth of the abnormal tissue in the breast tissue, a two-dimensional thermal image and a three-dimensional thermal image is generated respectively based on a plurality of intermediate temperature values. In an embodiment, the plurality of intermediate temperature values for both the two-dimensional and the three-dimensional images is estimated based on pre-defined model of the breast of the subject. The prediction system predicts the location and the depth of the abnormal tissue based on the two-dimensional thermal image and the three-dimensional thermal image of the breast tissue of the subject respectively.

FIG. 1 illustrates an exemplary environment for classifying health of breast tissues of a subject in accordance with some embodiments of the present disclosure.

As shown in FIG. 1, the environment 100 comprises a prediction system 101 connected through a communication network 107 to a device $103_1$, a device $103_2$, and a device $103_N$ (collectively called as plurality of devices 103). In an embodiment, the plurality of devices 103 may refer to a wearable device which may be worn by subjects. The prediction system 101 may also be connected to a database 105. In an embodiment, the plurality of devices 103 may include, but are not limited, to a brassiere. A person skilled in the art would understand that any other wearable devices not mentioned explicitly in the present disclosure, may also be used as the plurality of device 103. In an embodiment, the plurality of devices 103 comprises thermal sensors placed on each of the plurality of device 103, such that, the thermal sensors are in contact at pre-determined positions of breast of subjects. In an embodiment, the thermal sensors are used for measuring the temperature of the breast of the subject. In an embodiment, the prediction system 101 may include, but are not limited to, a laptop, a desktop computer, a Personal Digital Assistant (PDA), a notebook, a smartphone, a tablet, and any other computing devices. In an embodiment, the prediction system 101 predicts location and depth of an abnormal tissue in the breast tissue of the subject. In an embodiment, the abnormal tissue may refer to a condition where the tissue grows in an unusual pattern.

Whenever the breast tissue of a subject is classified to contain an abnormal tissue, a plurality of temperature values associated with the breast of the subject is received by the prediction system 101. In an embodiment, a device from the plurality of devices 103 may sense the temperature of the breast tissue of the subject for a pre-defined time duration and at pre-defined position. On receiving the plurality of temperature data, the prediction system 101 may estimate a plurality of intermediate temperature values, within the plurality of temperature values. The plurality of intermediate temperature values is estimated based on one of triangular patterns and rectangular patterns which are formed on a pre-defined model of the breast of the subject, thermal conductivity of the breast tissue, two-dimensional coordinates on at least one of the triangular patterns and the rectangular patterns and temperature values at steady state of the breast tissue of the subject. Using the plurality of intermediate temperature values and the plurality of temperature values, the prediction system 101 may generate a two-dimensional thermal image of the breast of the subject. In an embodiment, the two-dimensional thermal image is represented by one or more colors depending upon the plurality of temperature values and the plurality of intermediate temperature values. For example, a red color may imply a high temperature area and a blue color may imply a lower temperature area. In an embodiment, in the generated two-dimensional thermal image, lower part of each breast always shows a high temperature (red in colour) due to a fact that the subject is analysed in an upright position and hence sagging of the breast cannot be avoided. A correction may be applied as disclosed in description of FIG. 2a below to get an image without sagging of the breast. In an embodiment, the two-dimensional thermal image of the breast of the subject is generated based on at least one of a linear interpolation technique and a higher order interpolation technique. A person skilled in the art would understand that any other technique for generating two-dimensional thermal image, not mentioned in the present invention may also be used in the present disclosure. Further, based on the two-dimensional thermal image, the prediction system 101 predicts the location of the abnormal tissue in the breast. In an embodiment, the location of the abnormal tissue is predicted by the two-dimensional coordinates associated with an abnormal temperature value, among the plurality of temperature values and the plurality of intermediate temperature values. In an embodiment, the plurality of intermediate temperature values is determined using at least one of Finite Element Method (FEM) and Finite Volume Method (FVM) technique. A person skilled in the art would understand that any other technique for determining intermediate temperature values, not mentioned in the present invention may also be used in the present disclosure.

Further, to determine depth of the abnormal tissue, the prediction system 101 may estimate a plurality of intermediate temperature values within the plurality of temperature values. The plurality of intermediate temperature values is estimated based on one of tetrahedral patterns and hexahedral patterns formed on a predefined model of the breast of the subject, density value, thermal conductivity of the tissue, blood perfusion rate, specific heat capacity of the blood, three-dimensional coordinates on at least one of the tetrahedral patterns and the hexahedral patterns, arterial temperature and metabolic heat generation value in a normal and in an abnormal tissue. Once the plurality of intermediate temperature values is estimated, the prediction system 101 generates a three-dimensional thermal image of the breast tissue of the subject using the plurality of intermediate temperature values, the plurality of temperature values and an error parameter. In an embodiment, the error parameter is iteratively calculated based on the plurality of temperature values received from the device and the plurality of intermediate temperature values until when the computed error parameter attains a predefined acceptable limit. In an embodiment, the three-dimensional thermal image of the breast of the subject is generated based on at least one of linear interpolation and quadratic interpolation techniques. A person skilled in the art would understand that any other technique for generating three-dimensional image, not mentioned in the present disclosure may also be used in the present disclosure. Further, based on the three-dimensional thermal image, the prediction system 101 predicts depth of the abnormal tissue in the breast tissue of the subject. In an embodiment, the depth of the abnormal tissue is predicted by the three-dimensional coordinates of a temperature value associated with a higher temperature value among the plurality of temperature values and the plurality of intermediate temperature values. In an embodiment, the prediction system 101 classifies the breast tissue of the subject into corresponding category based on a relative score. The relative score is generated based on a pre-defined data of healthy tissues and the plurality of temperature values associated with the subject.

The prediction system 101 comprises an I/O Interface 109, a memory 111 and a processor 113. The I/O interface 109 may be configured to receive the plurality of temperature values associated with the breast temperature of the subject.

The received information from the I/O interface 109 is stored in the memory 111. The memory 111 is communicatively coupled to the processor 113 of the prediction system 101. The memory 111 also stores processor instructions which cause the processor 113 to execute the instructions for predicting location and depth of abnormal tissue in breast tissue of the subject.

Figure 2A:
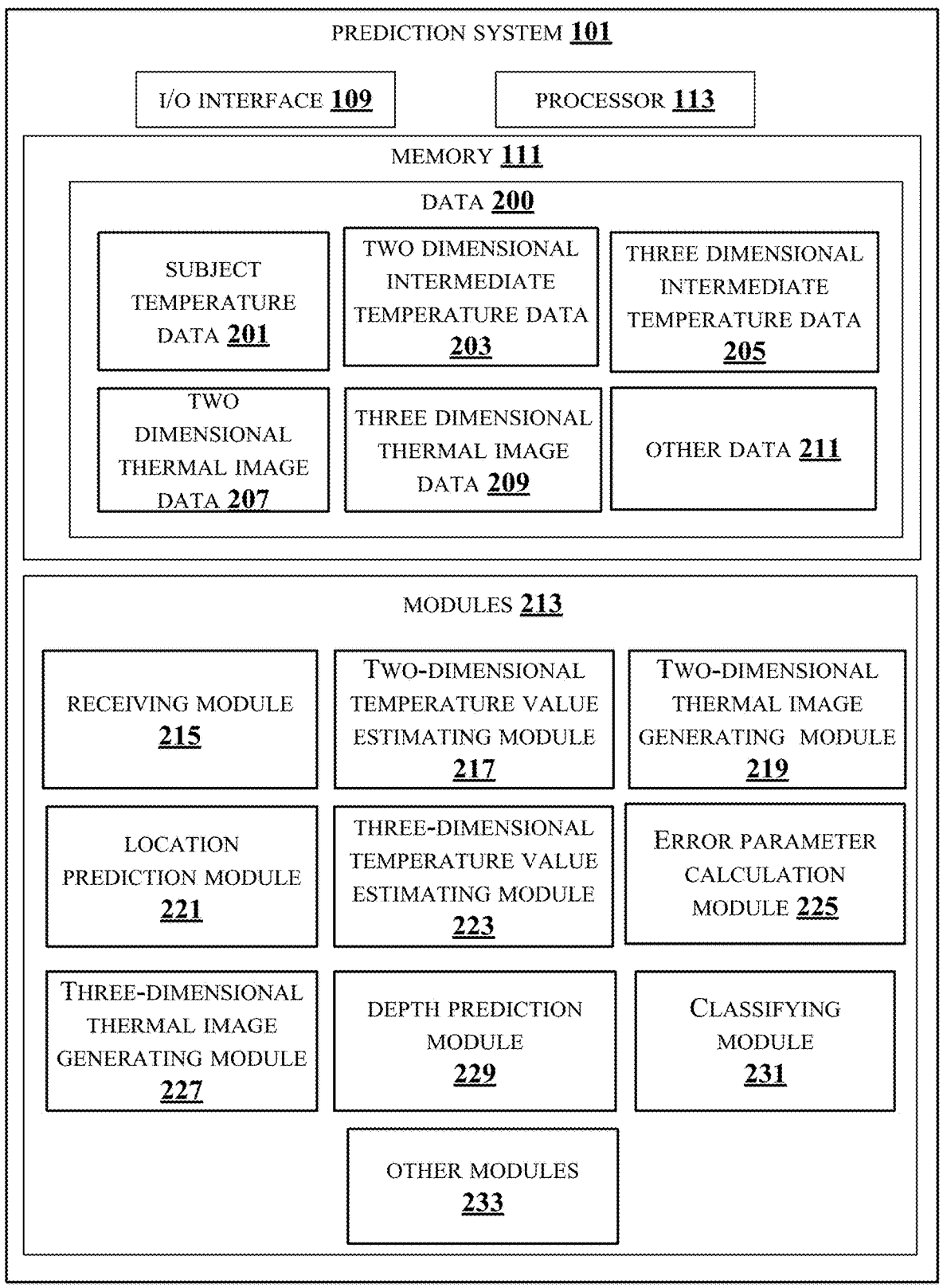
FIG. 2a shows a detailed block diagram of a prediction system in accordance with some embodiments of the present disclosure.

FIG. 2a shows a detailed block diagram of prediction system in accordance with some embodiments of the present disclosure.

Data 200 and one or more modules 213 of the prediction system 101 are described herein in detail. In an embodiment, the data 200 comprises subject temperature data 201, two-dimensional intermediate temperature data 203, three-dimensional intermediate temperature data 205, two-dimensional thermal image data 207, three-dimensional thermal image data 209 and other data 211.

The subject temperature data 201 may comprise the plurality of temperature values associated with the breast tissue of the subject. The subject temperature data 201 may comprise details regarding the two-dimensional coordinates and three-dimensional coordinates of the breast tissue of the subject.

The two-dimensional intermediate temperature data 203 may include the plurality of intermediate temperature values. The two-dimensional intermediate temperature values are estimated based on one of the triangular patterns and rectangular patterns formed on a pre-defined model of the breast of the subject, thermal conductivity of the breast tissue, two-dimensional coordinates on at least one of the triangular patterns and the rectangular patterns and temperature values at steady state of the breast tissue of the subject.

The three-dimensional intermediate temperature data 205 may include the plurality of intermediate temperature values associated with three-dimensional view of the breast of the subject. The three-dimensional intermediate temperature values are estimated based on one of the tetrahedral patterns and hexahedral patterns formed on a predefined model of the breast of the subject, density value, thermal conductivity of the tissue, blood perfusion rate, specific heat capacity of the blood, the three-dimensional coordinates on at least one of the tetrahedral patterns and the hexahedral patterns, arterial temperature and metabolic heat generation value in a normal and in an abnormal tissue.

The two-dimensional thermal image data 207 may comprise the two-dimensional thermal image of the breast tissue of the subject. The two-dimensional thermal image is represented by one or more colors depending upon the plurality of temperature values and the plurality of intermediate temperature values.

The three-dimensional thermal image data 209 may comprise the three-dimensional thermal image of the breast tissue of the subject. The three-dimensional thermal image is represented by one or more colors depending upon the plurality of temperature values and the plurality of intermediate temperature values.

The other data 211 may store data, including temporary data and temporary files, generated by the one or more modules 213 for performing the various functions of the prediction system 101.

In an embodiment, the data 200 in the memory 111 are processed by the one or more modules 213 of the prediction system 101. As used herein, the term module may refers to an application specific integrated circuit (ASIC), an electronic circuit, a field-programmable gate arrays (FPGA), Programmable System-on-Chip (PSoC), a combinational logic circuit, and/or other suitable components that provide the described functionality. The said modules 213 when configured with the functionality defined in the present disclosure will result in a novel hardware.

In one implementation, the one or more modules 213 may include, but are not limited to, a receiving module 215, a Two-Dimensional (2D) temperature value estimating module 217, a Two-Dimensional (2D) thermal image generating module 219, a location prediction module 221, a Three-Dimensional (3D) temperature value estimating module 223, an error parameter calculation module 225, a Three-Dimensional (3D) thermal image generating module 227, a depth prediction module 229 and a classifying module 231. The one or more modules 213 may also comprise other modules 233 to perform various miscellaneous functionalities of the prediction system 101. It will be appreciated that such modules 213 may be represented as a single module or a combination of different modules 213.

The receiving module 215 may receive the plurality of temperature values from the device 103 worn by the subject. In an embodiment, the plurality of temperature data from the device 103 is received in an electrical signal form. In an embodiment, the temperature data may be identified in association for position of the thermal sensors on the breast of the subject.

The 2D temperature value estimating module 217 may estimate the plurality of intermediate temperature values within the plurality of temperature values. In an embodiment, the 2D temperature value estimating module 217 may use the pre-defined model of the breast tissue of the subject. In an embodiment, the pre-defined model may include triangular patterns and rectangular patterns. In an embodiment, patterns of different types suiting the need such as triangular or rectangular elements with linear or quadratic interpolation functions can be used to obtain the plurality of intermediate temperature values. For instance, 1200-1500 linear triangular elements are used to construct one model with 400-800 nodes. Further, the 2D temperature value estimating module 217 may also estimate the plurality of intermediate temperature values, based on the thermal conductivity of the breast tissue, the two-dimensional coordinates on at least one of the triangular patterns and the rectangular patterns and temperature values at steady state of the breast tissue of the subject. In an embodiment, a governing equation for a steady state temperature distribution over a region of interest is mathematically expressed as shown below in equation 1.

$$K\nabla^2 T = 0 \qquad (1)$$

where K is the thermal conductivity
T is the temperature $$\nabla^2 T = \frac{\partial^2 T}{\partial x^2} + \frac{\partial^2 T}{\partial y^2} \text{ for a } 2D \text{ approximation.} \qquad (2)$$

Figure 2B:
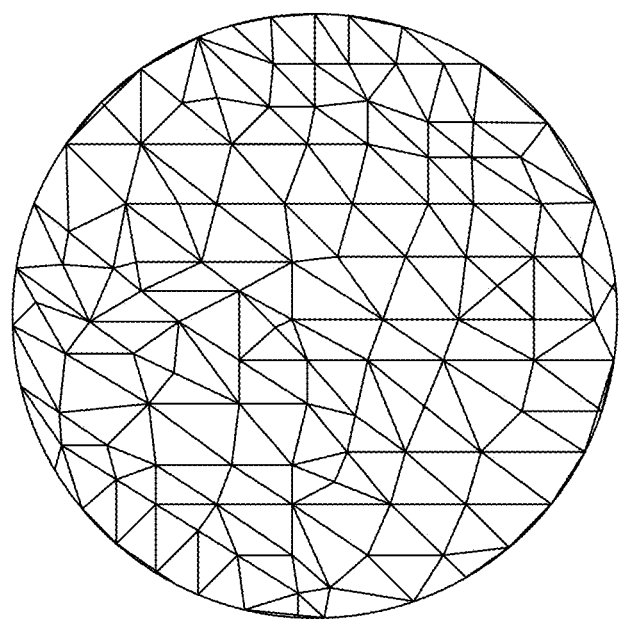
FIG. 2b shows an exemplary representation of a breast model based on triangular pattern in accordance with some embodiments of the present disclosure.

In an embodiment, the equation (1) may be solved completely, only if the necessary boundary conditions are also specified. The boundary conditions may be taken from the plurality of temperature values obtained from device 103. The 2D temperature value estimating module 217 estimates the plurality of intermediate temperature values based on the one of triangular patterns and rectangular patterns formed on a pre-defined model of the breast of the subject, thermal conductivity of the breast tissue, two-dimensional coordinates on at least one of the triangular patterns and the rectangular patterns and temperature values at steady state of the breast tissue of the subject. In an embodiment, the 2D temperature value estimating module 217 may estimate the plurality of intermediate temperature values using at least one of Finite Element Method (FEM) and Finite Volume Method (FVM) technique. A person skilled in the art would understand that any other technique, not mentioned explicitly for estimating intermediate values, may also be used in the present disclosure. In an embodiment, to estimate the intermediate temperature distribution over the breast, the pre-defined model of the breast is discretized (meshed) by linear triangular elements, with each element consisting of pre-defined nodes. FIG. 2b shows an exemplary representation of a breast model based on triangular pattern in accordance with some embodiments of the present disclosure. In an embodiment, the discretization generates details such as, nodes which constitute each element and coordinate information of all the nodes. In an embodiment, connectivity between neighboring elements may be established through nodes thereby conforming the continuity of solution across the element boundaries. Table 1 below shows different meshing.

TABLE 1

| | Mesh Components | |
|---|---|---|
| Meshed Levels | Elements | Nodes |
| LEVEL 1 | 104 | 65 |
| LEVEL 2 | 414 | 232 |
| LEVEL 3 | 1374 | 732 |
| LEVEL 4 | 5492 | 2835 |
| LEVEL 5 | 49428 | 24979 |

Figure 2C:
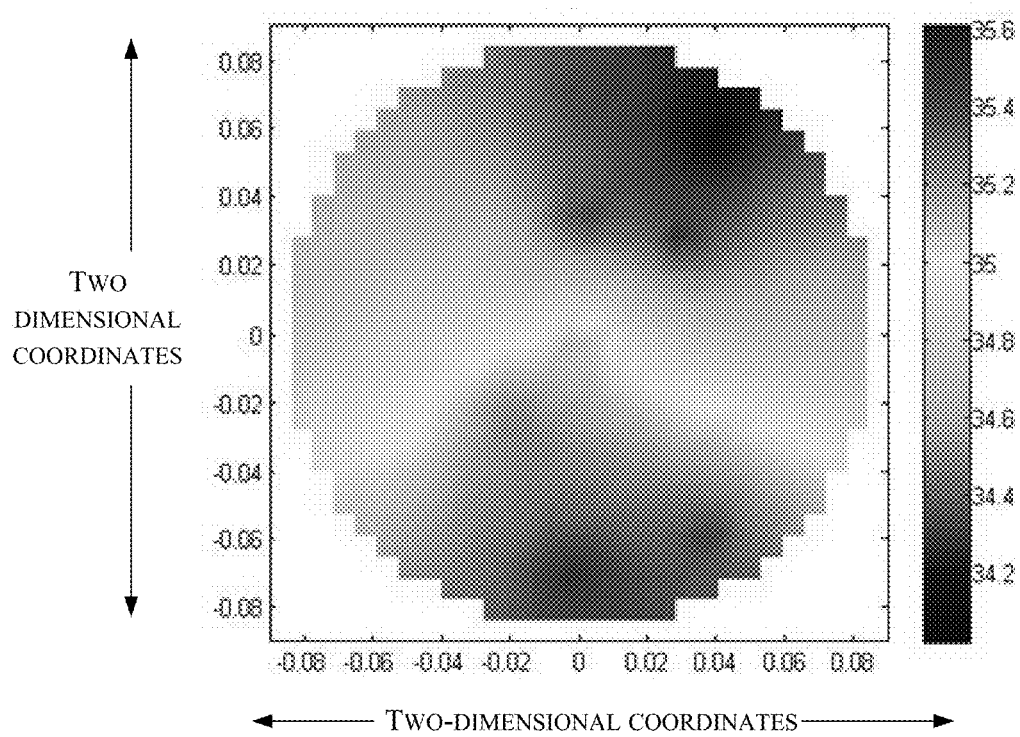
FIG. 2c shows an exemplary representation of a two-dimensional thermal image of a breast of a subject in accordance with some embodiments of the present disclosure.

The Two-Dimensional (2D) thermal image generating module 219 generates the two-dimensional thermal image of the breast of the subject based on the plurality of the 2D temperature values and the plurality of intermediate temperature values. In an embodiment, the two-dimensional thermal image of the breast of the subject is generated based on at least one of a linear interpolation technique and a higher order interpolation technique. In an embodiment, the two-dimensional thermal image is represented by one or more colors depending upon the plurality of temperature values and the plurality of intermediate temperature values. FIG. 2c shows an exemplary representation of a two-dimensional thermal image of a breast of a subject in accordance with some embodiments of the present disclosure. As shown in FIG. 2c, the breast image of the subject is represented by gradation of colors from red color to blue color. The red color indicates higher temperature as compared to the blue color.

The location prediction module 221 predicts the location of the abnormal tissue in the breast tissue of the subject based on the two-dimensional thermal image. The location prediction module 221 predicts the location of the abnormal tissue based on the two-dimensional coordinates associated with an abnormal temperature value, among the plurality of temperature values and the plurality of intermediate temperature values.

The three-Dimensional (3D) temperature value estimating module 223 estimates the plurality of intermediate temperature values within the plurality of temperature values. In an embodiment, the 3D temperature value estimating module 223 may use the pre-defined model of the breast tissue of the subject. In an embodiment, the pre-defined model may include at least one of the tetrahedral patterns and hexahedral patterns formed on a predefined model of the breast of the subject. Further, the 3D temperature value estimating module 223 estimates the 3D intermediate temperature values based on the density value, the thermal conductivity of the tissue, the blood perfusion rate, the specific heat capacity of the blood, three-dimensional coordinates on at least one of the tetrahedral patterns and the hexahedral patterns, arterial temperature and metabolic heat generation value in a normal and in an abnormal tissue. In an embodiment, the discrete temperature values measured on pre-defined positions of the breast tissue is converted to a 3D thermal profile of the breast tissue of the subject using a three-dimensional Pennes bioheat transfer equation which is given below in equation (2).

$$\rho C \frac{\partial T}{\partial t} = K \nabla^2 T + W_b C_b (T_a - T) + Q_m \qquad (2)$$

Where $$\nabla^2 T = \frac{\partial T}{\partial x^2} + \frac{\partial^2 T}{\partial y^2} + \frac{\partial^2 T}{\partial z^2}$$

$\rho$=density,
C=specific heat capacity,
K=thermal conductivity of the tissue,
$W_b$=is the blood perfusion rate,
$C_b$=specific heat capacity of the blood,
$T_a$=arterial temperature,
$Q_m$=metabolic heat generation.

At steady state, the above equation (2) becomes $$K\nabla^2 T + W_b C_b (T_a - T) + Q_m = 0 \qquad (3)$$

In an embodiment, the metabolic activity in the abnormal tissue may be different from that of a normal tissue. In such case, equation (3) can be re-written as:

$$K\nabla^2 T + W_b C_b (T_a - T) + Q_{nm} = Q_{mm} = 0 \qquad (4)$$

where $Q_{nm}$=metabolic heat generation in normal tissue $Q_{mem}$ metabolic heat generation abnormal tissue.

Further, the three-Dimensional (3D) temperature value estimating module 223 may estimate the plurality of intermediate temperature values using at least one of a Finite Element Method (FEM) and a Finite Volume Method (FVM) technique. In an embodiment, the FEM is a method used for solving a differential equation with associated boundary conditions by approximating continuous quantities as a set of quantities at discrete points which forms a grid or a mesh. The FEM is used to solve the above equations over the domain (breast). In an embodiment, the breast tissue under consideration is divided into small pieces and treated as isolated, interacting sections called elements. The elements are simple-shaped and connected at points called nodes. Further, the three-Dimensional (3D) temperature value estimating module 223 estimates the temperature distribution over the breast by discretization of the breast tissue (meshed) by tetrahedral or cubic elements depending upon the size of the breast. In an embodiment, meshing generates details such as the nodes which constitute each element and coordinate information of all the nodes. Connectivity between neighboring elements is established through nodes thereby conforming the continuity of solution across the element boundaries. Further, for solving the equation using FEM, the values of the numerical parameters are, arterial temperature ($T_a$) taken as 37° C., specific heat of the blood ($C_b$)=3500 J/kg° C., metabolic heat generation in normal tissue ($Q_{nm}$) as 43800 w/m³, thermal conductivity of the tissue (K) as 0.5, W/m° C. and blood perfusion rate ($W_b$) as $19 \times 10^{-5}$ ml/100 g min for normal tissues. In case, if any abnormality at any point arises, the $W_b$ may be different at that place due to higher metabolic activities.

The error parameter calculation module 225 calculates the error parameter based on the plurality of temperature values received from the device and the plurality of intermediate temperature values. In an embodiment, by minimizing the error parameter, the three-dimensional heat distribution and the blood perfusion rate are obtained. The error parameter calculation module 225 calculates the error parameter continuously until the computed error parameter is lesser than a pre-defined value. In an embodiment, the position with high metabolic heat generation and high blood perfusion rate indicates abnormal tissue.

The Three-Dimensional (3D) thermal image generating module 227 generates the three-dimensional thermal image using the plurality of temperature values and the plurality of intermediate temperature values and the error parameter. In an embodiment, the 3D thermal image is represented by one or more colors depending on the plurality of temperature values and the plurality of intermediate temperature values. The three-Dimensional (3D) thermal image generating module 227 generates the three-dimensional thermal image of the breast of the subject based on at least one of linear interpolation and quadratic interpolation techniques.

The depth prediction module 229 predicts the depth of the abnormal tissue from the 3D thermal image of the breast tissue of the subject. The depth prediction module 229 may predict the depth of the abnormal tissue using the three-dimensional coordinates of a temperature value which is associated with a higher temperature value among the plurality of temperature values and the plurality of intermediate temperature values.

The classifying module 231 classifies the breast tissue of the subject into corresponding category based on a relative score. In an embodiment, relative score is generated based on pre-defined data of healthy tissues and the plurality of temperature values associated with the subject. In an embodiment, a theoretical model to represent the correlation of left and right breast tissue temperature is developed by two-degree polynomial. In an embodiment, the pre-defined data from healthy volunteer is used for healthy person's theoretical model and the subject data is taken for subject theoretical model. The classifying module 231 provides the unknown temperature data from the pre-defined data (of healthy volunteer) to the models to obtain theoretical median temperatures. Further, the classifying module 231 compares the experimentally determined temperature data and the theoretically determined data to get an error value P and H for subject theoretical model and healthy person's theoretical model respectively. When the error value P is minimum, the possibility of abnormality of the breast tissue of the subject is high. Similarly, when the H value is minimum the subject may be healthy. In an embodiment, the classifying module 231 classifies the breast tissue of the subject into one of negative, to be screened, probably benign, suspicious and highly Suspicious. The classification into negative category indicates that the temperature data is similar to healthy breast data. The classification into "to be screened" category indicates examination may be required once in a year as the temperature data may have slight deviation from the normal one. The classification into "probably benign" indicate an abnormality inside the breast. The classification into suspicious category indicates abnormality leading to tumor. The highly suspicious category indicates requirement for immediate treatment.

Figure 3A:
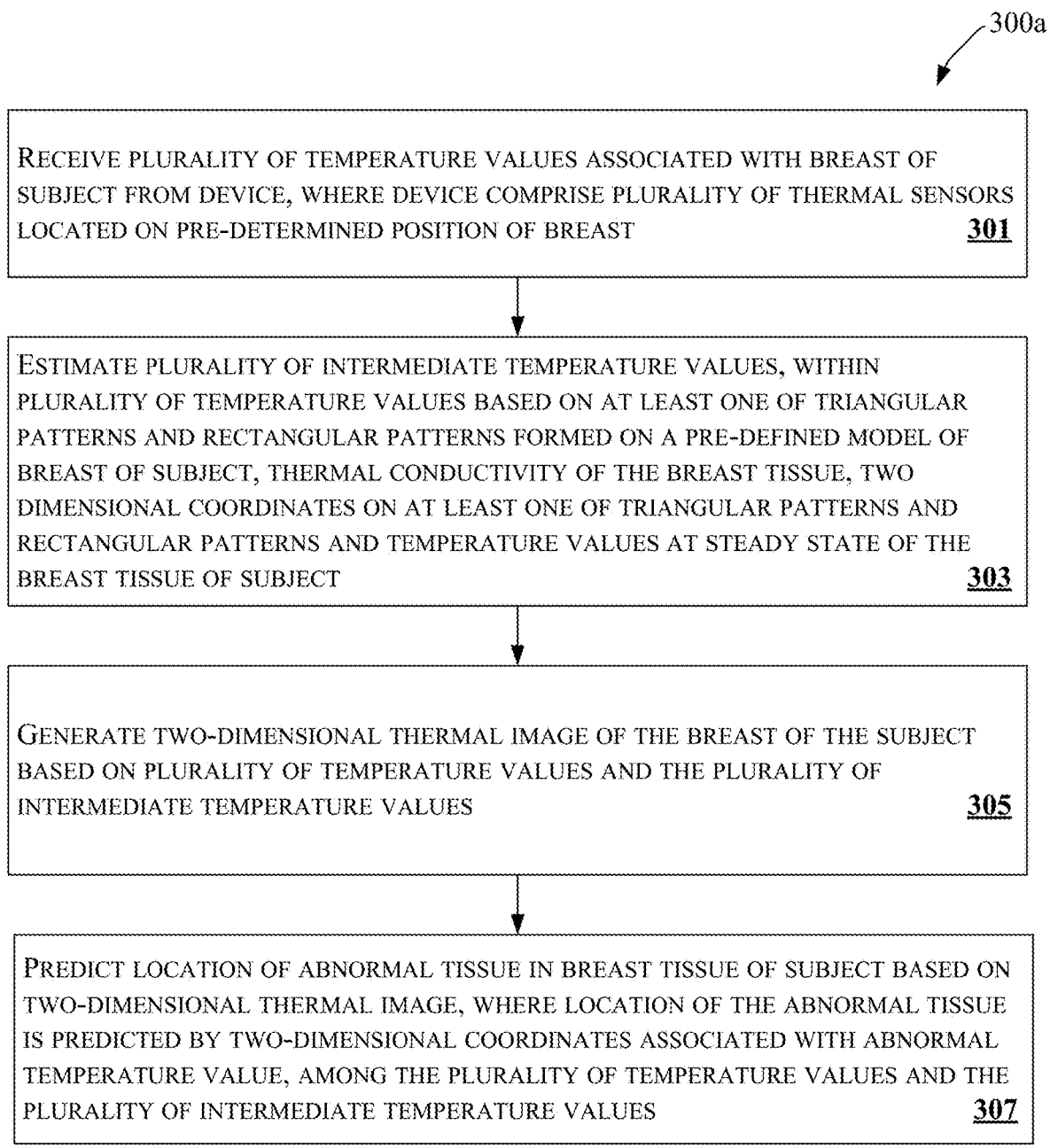
FIG. 3a illustrates a flowchart showing a method for predicting location of an abnormal tissue in breast tissue of a subject in accordance with some embodiments of present disclosure.

FIG. 3a illustrates a flowchart showing a method for predicting location of an abnormal tissue in breast tissue of a subject in accordance with some embodiments of present disclosure.

As illustrated in FIG. 3a, the method 300a comprises one or more blocks for predicting location of an abnormal tissue in breast tissue of a subject. The method 300a may be described in the general context of computer executable instructions. Generally, computer executable instructions can include routines, programs, objects, components, data structures, procedures, modules, and functions, which perform particular functions or implement particular abstract data types.

The order in which the method 300a is described is not intended to be construed as a limitation, and any number of the described method blocks can be combined in any order to implement the method. Additionally, individual blocks may be deleted from the methods without departing from scope of the subject matter described herein. Furthermore, the method can be implemented in any suitable hardware, software, firmware, or combination thereof.

At block 301, the plurality of temperature values associated with a breast of a subject is received, by the receiving module 215, from the device 103. The device 103 comprises the plurality of thermal sensors locatable on the pre-determined positions of the breast of the subject.

At block 303, the plurality of intermediate temperature values is estimated, by the two-dimensional temperature value estimating module 217, within the plurality of temperature values. The plurality of intermediate temperature values is estimated based on at least one of triangular patterns and rectangular patterns formed on a pre-defined model of the breast of the subject, thermal conductivity of the breast tissue, two-dimensional coordinates on at least one of the triangular patterns and the rectangular patterns and temperature values at steady state of the breast tissue of the subject.

At block 305, the two-dimensional thermal image of the breast of the subject is generated, by the two-dimensional thermal image generating module 219 based on the plurality of the temperature values and the plurality of intermediate temperature values.

At block 307, the location of the abnormal tissue is predicted in the breast tissue of the subject by the location prediction module 221, based on the two-dimensional thermal image. The location of the abnormal tissue is predicted by the two-dimensional coordinates associated with the abnormal temperature value, among the plurality of temperature values and the plurality of intermediate temperature values.

Figure 3B:
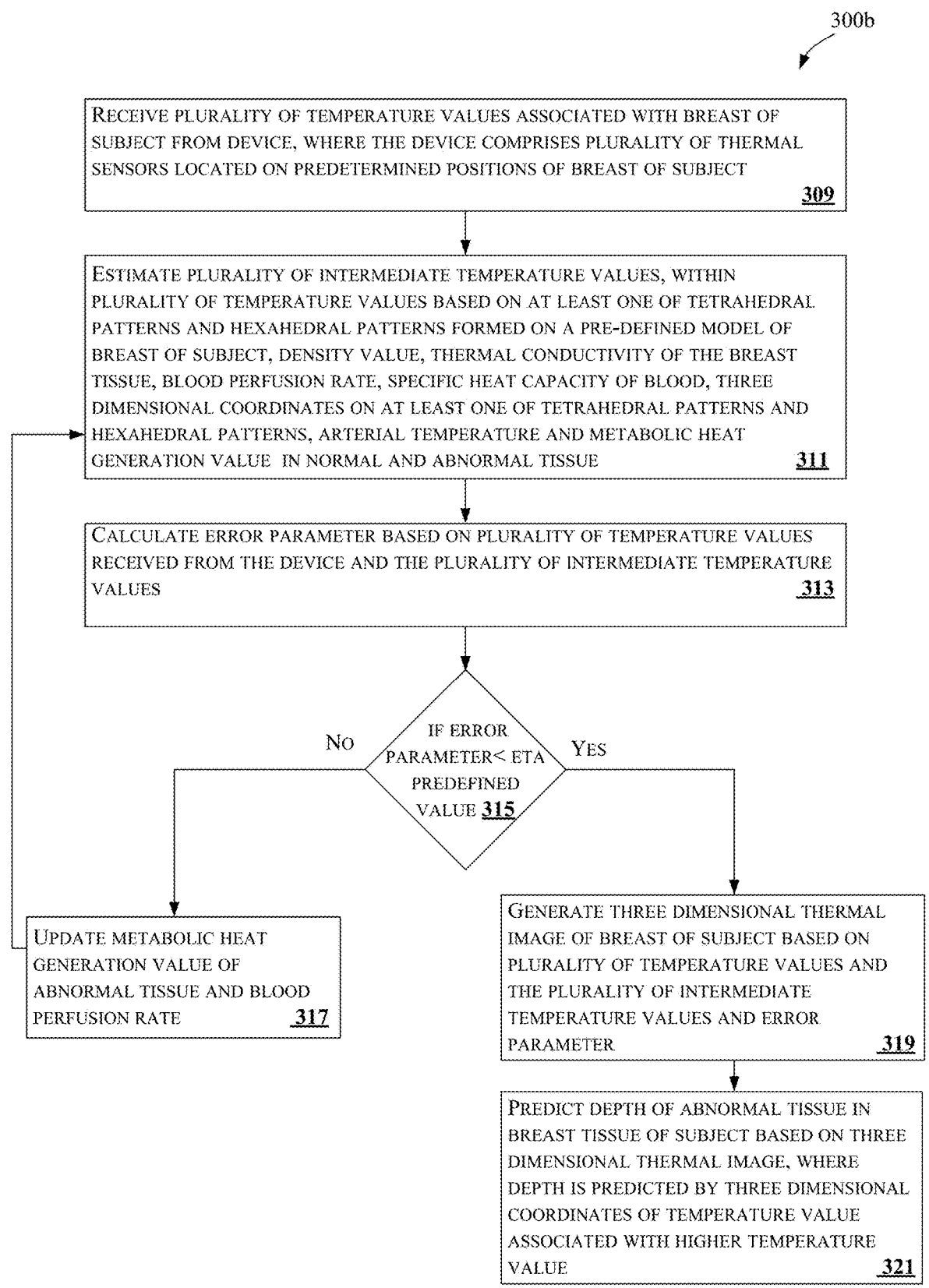
FIG. 3b illustrates a flowchart showing a method for predicting depth of an abnormal tissue in breast tissue of a subject in accordance with some embodiments of present disclosure.

FIG. 3b illustrates a flowchart showing a method for predicting depth of an abnormal tissue in breast tissue of a subject in accordance with some embodiments of present disclosure.

As illustrated in FIG. 3b, the method 300b comprises one or more blocks for predicting depth of an abnormal tissue in breast tissue of a subject. The method 300b may be described in the general context of computer executable instructions. Generally, computer executable instructions can include routines, programs, objects, components, data structures, procedures, modules, and functions, which perform particular functions or implement particular abstract data types.

The order in which the method 300b is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 309, the plurality of temperature values associated with the breast of the subject is received, by the receiving module 215 from the device 103. The device 103 may comprise the plurality of thermal sensors locatable on pre-determined positions of the breast of the subject.

At block 311, the plurality of intermediate temperature values within the plurality of temperature values is estimated, by the three-dimensional temperature value estimating module 223. The intermediate temperature values are estimated based on at least one of tetrahedral patterns and hexahedral patterns formed on a predefined model of the breast of the subject, density value, thermal conductivity of the tissue, blood perfusion rate, specific heat capacity of the blood, three-dimensional coordinates on at least one of the tetrahedral patterns and the hexahedral patterns, arterial temperature and metabolic heat generation value in a normal and in an abnormal tissue.

At block 313, the error parameter is calculated, by the error calculation module 225 based on the plurality of temperature values received from the device 103 and the plurality of intermediate temperature values.

At block 315, the error parameter is compared with the pre-defined value, by the error calculation module 225. In case, the error parameter is greater than the pre-defined value, the method moves to block 317. Alternatively, if the error parameter is lesser than the pre-defined values, the method moves to block 319.

At block 317, the metabolic heat generation value of abnormal tissue ($Q_{mm}$) and blood perfusion rate ($W_b$) are updated by the error calculation module 225. On updating, the updated metabolic heat generation value of abnormal tissue ($Q_{mm}$) and blood perfusion rate are used for estimating new plurality of intermediate temperature values.

At block 319, the three-dimensional thermal image of the breast of the subject is generated, by the three-dimensional thermal image generating module 227, based on the plurality of temperature values and the plurality of intermediate temperature values and an error parameter.

At block 321, the depth of the abnormal tissue in the breast tissue of the subject is predicted, by the depth prediction module 229, based on the three-dimensional thermal image. In an embodiment, the depth of the abnormal tissue is predicted by the three-dimensional coordinates of the temperature value associated with the higher temperature value among the plurality of temperature values and the plurality of intermediate temperature values.

Computing System

Figure 4:
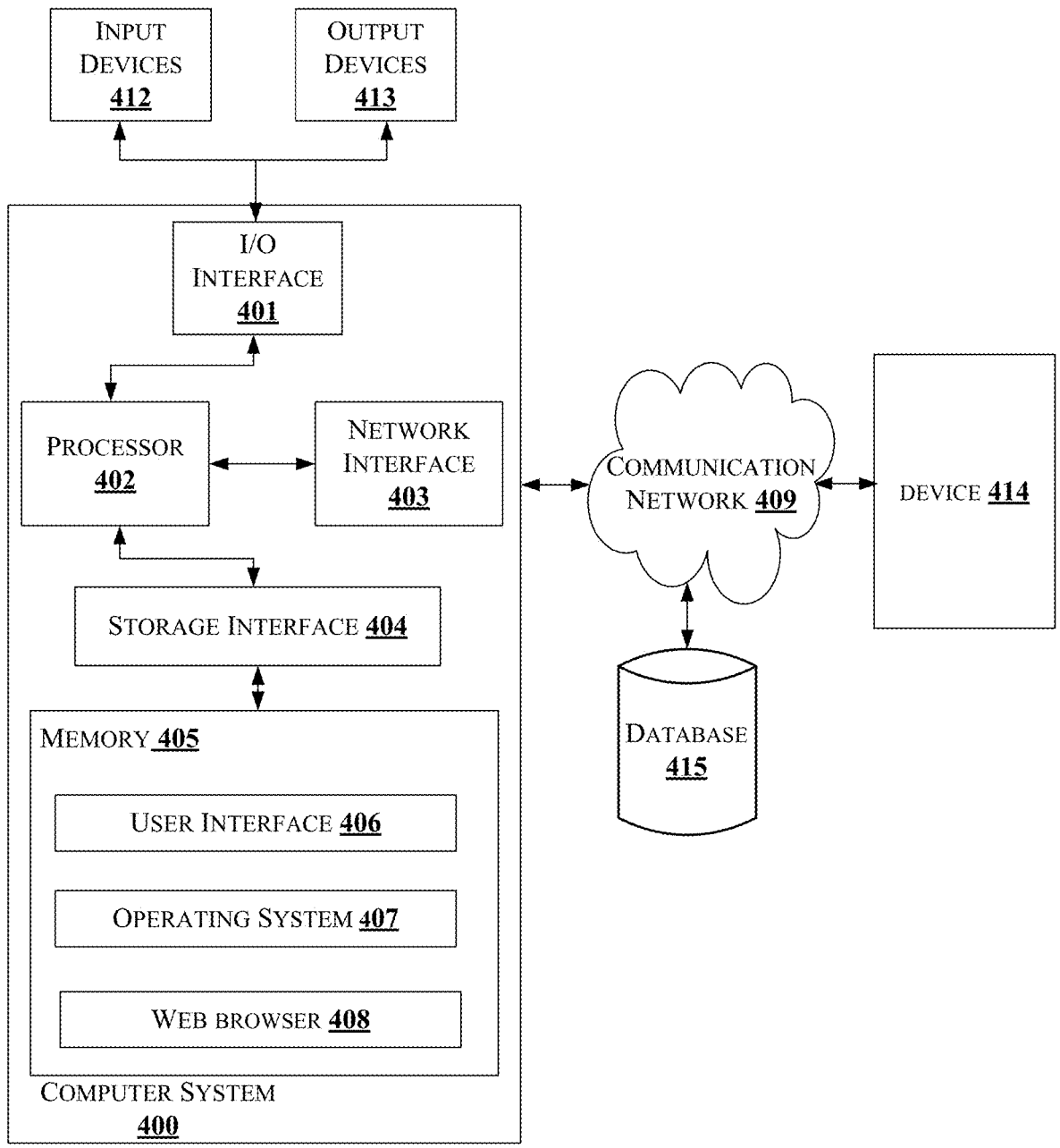
FIG. 4 illustrates a block diagram of an exemplary computer system for implementing embodiments consistent with the present disclosure.

FIG. 4 illustrates a block diagram of an exemplary computer system 400 for implementing embodiments consistent with the present disclosure. In an embodiment, the computer system 400 is used to implement the prediction system 101. The computer system 400 may comprise a central processing unit ("CPU" or "processor") 402. The processor 402 may comprise at least one data processor for predicting location and depth of abnormal tissue in a breast tissue of a subject. The processor 402 may include specialized processing units such as, integrated system (bus) controllers, memory management control units, floating point units, graphics processing units, digital signal processing units, etc.

The processor 402 may be disposed in communication with one or more input/output (I/O) devices (not shown) via I/O interface 401. The I/O interface 401 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 401, the computer system 400 may communicate with one or more I/O devices. For example, the input device may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output device may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc.

In some embodiments, the computer system 400 consists of a prediction system 101. The processor 402 may be disposed in communication with the communication network 409 via a network interface 403. The network interface 403 may communicate with the communication network 409. The network interface 403 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 409 may include, without limitation, a direct interconnection, local area network (LAN), wide area network (WAN), wireless network (e.g., using Wireless Application Protocol), the Internet, etc. Using the network interface 403 and the communication network 409, the computer system 400 may communicate with a device 414 and a database 415. The network interface 503 may employ connection protocols include, but not limited to, direct connect, Ethernet (e.g., twisted pair 10/100/1000 Base T), transmission control protocol/internet protocol (TCP/IP), token ring, IEEE 802.11a/b/g/n/x, etc.

The communication network 409 includes, but is not limited to, a direct interconnection, an e-commerce network, a peer to peer (P2P) network, local area network (LAN), wide area network (WAN), wireless network (e.g., using Wireless Application Protocol), the Internet, Wi-Fi and such. The first network and the second network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the first network and the second network may include a variety of network devices, including routers, bridges, servers, computing devices, storage devices, etc.

In some embodiments, the processor 402 may be disposed in communication with a memory 405 (e.g., RAM, ROM, etc. not shown in FIG. 4) via a storage interface 404. The storage interface 404 may connect to memory 405 including, without limitation, memory drives, removable disc drives, etc., employing connection protocols such as, serial advanced technology attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, user interface 406, an operating system 407 etc. In some embodiments, computer system 400 may store user/application data 406, such as, the data, variables, records, etc., as described in this disclosure. Such databases may be implemented as fault-tolerant, relational, scalable, secure databases such as Oracle or Sybase.

The operating system 407 may facilitate resource management and operation of the computer system 400. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, non-volatile memory, hard drives, CD ROMs, DVDs, flash drives, disks, and any other known physical storage media.

An embodiment of the present disclosure detects cancer in the breast of the subject at early stages without any radiation exposure and pain.

An embodiment of the present disclosure can be used for younger women having dense breast.

An embodiment of the present disclosure provides estimated location and depth of abnormal tissue in breast tissue of the subject.

The present disclosure provides a highly cost effective, user friendly and portable device for detecting cancer in the breast of the subject.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may comprise media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. Further, non-transitory computer-readable media comprise all computer-readable media except for a transitory. The code implementing the described operations may further be implemented in hardware logic (e.g., an integrated circuit chip, Programmable Gate Array (PGA), Application Specific Integrated Circuit (ASIC), etc.).

Still further, the code implementing the described operations may be implemented in "transmission signals", where transmission signals may propagate through space or through a transmission media, such as, an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a non-transitory computer readable medium at the receiving and transmitting stations or devices. An "article of manufacture" comprises non-transitory computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the invention, and that the article of manufacture may comprise suitable information bearing medium known in the art.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIGS. 3a and 3b show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 100 | Environment |
| 101 | Prediction system |
| 103 | Plurality of devices |
| 105 | Database |
| 107 | Communication network |
| 109 | I/O interface |
| 111 | Memory |
| 113 | Processor |
| 200 | Data |
| 201 | Subject temperature data |
| 203 | Two-dimensional intermediate temperature data |
| 205 | Three-dimensional intermediate temperature data |
| 207 | Two-dimensional thermal image data |
| 209 | Three-dimensional thermal image data |
| 211 | Other data |
| 213 | Modules |
| 215 | Receiving module |
| 217 | Two-dimensional temperature value estimating module |
| 219 | Two-dimensional thermal image generating module |
| 221 | Location prediction module |
| 223 | Three-dimensional temperature value estimating module |
| 225 | Error parameter calculation module |
| 227 | Three-dimensional thermal image generating module |
| 229 | Depth prediction module |
| 231 | Classifying module |
| 233 | Other modules |

We claim:

1. A method for predicting depth of abnormal tissue in a breast tissue of a subject, the method comprising:

receiving, by a prediction system (101), a plurality of temperature values associated with a breast of the subject from a device, wherein the device comprises a plurality of thermal sensors locatable on pre-determined positions of the breast of the subject, wherein each temperature value is represented by a node that corresponds to at least one pre-determined position of the breast of the subject;

estimating, by the prediction system (101), a plurality of intermediate temperature values within the plurality of temperature values, based on density value, thermal conductivity of the breast tissue, blood perfusion rate, specific heat capacity of the blood, arterial temperature, metabolic heat generation value in a normal and in an abnormal tissue, at least one of tetrahedral patterns and hexahedral patterns formed on a predefined model of the breast of the subject, and three dimensional coordinates on at least one of the tetrahedral patterns and the hexahedral patterns;

generating, by the prediction system (101), a three-dimensional thermal image of the breast of the subject based on the plurality of temperature values and the plurality of intermediate temperature values and an error parameter; and predicting, by the prediction system (101), depth of the abnormal tissue in the breast tissue of the subject based on, the three-dimensional thermal image, wherein the depth of the abnormal tissue is predicted by the three-dimensional coordinates of a temperature value associated with a higher temperature value among the plurality of temperature values and the plurality of intermediate temperature values.

2. The method as claimed in claim 1, wherein the plurality of intermediate temperature values is determined using at least one of a Finite Element Method (FEM) and a Finite Volume Method (FVM) technique.

3. The method as claimed in claim 1, wherein the error parameter is iteratively calculated based on the plurality of temperature values received from the device and the plurality of intermediate temperature values.

4. The method as claimed in claim 1, wherein the metabolic heat generation value in the abnormal tissue and the blood perfusion rate are updated when the error parameter is greater than a pre-defined value.

5. The method as claimed in claim 1, wherein the three-dimensional thermal image is represented by one or more colors depending on the plurality of temperature values and the plurality of intermediate temperature values.

6. The method as claimed in claim 1, wherein the three-dimensional thermal image of the breast of the subject is generated based on at least one of linear interpolation and quadratic interpolation techniques.

7. The method as claimed in claim 1 further comprising classifying the breast tissue of the subject into corresponding category based on a relative score, wherein the relative score is generated based on a pre-defined data of healthy tissues and the plurality of temperature values associated with the subject.

8. A prediction system (101) for predicting depth of abnormal tissue in a breast tissue of a subject, comprising:
a processor (113); and
a memory communicatively coupled to the processor, wherein the memory stores processor instructions, which, on execution, causes the processor to:
receive a plurality of temperature values associated with a breast of the subject from a device, wherein the device comprises a plurality of thermal sensors locatable on pre-determined positions of the breast of the subject, wherein each temperature value is represented by a node that corresponds to at least one pre-determined position of the breast of the subject;
estimate a plurality of intermediate temperature values within the plurality of temperature values, based on density value, thermal conductivity of the breast tissue, blood perfusion rate, specific heat capacity of the blood, arterial temperature, metabolic heat generation value in a normal and in an abnormal tissue, at least one of tetrahedral patterns and hexahedral patterns formed on a predefined model of the breast of the subject, and three dimensional coordinates on at least one of the tetrahedral patterns and the hexahedral patterns;

generate a three-dimensional thermal image of the breast of the subject based on the plurality of temperature values and the plurality of intermediate temperature values and an error parameter; and;

predict depth of the abnormal tissue in the breast tissue of the subject based on, the three-dimensional thermal image, wherein the depth of the abnormal tissue is predicted by the three-dimensional coordinates of a temperature value associated with a higher temperature value among the plurality of temperature values and the plurality of intermediate temperature values.

9. The prediction system (101) as claimed in claim 8, wherein the processor (113) determines the plurality of intermediate temperature values using at least one of a Finite Element Method (FEM) and a Finite Volume Method (FVM) technique.

10. The prediction system (101) as claimed in claimed 8, wherein the processor (113) calculates the error parameter iteratively based on the plurality of temperature values received from the device and the plurality of intermediate temperature values.

11. The prediction system (101) as claimed in claim 8, wherein the processor (113) updates the metabolic heat generation value in the abnormal tissue and the blood perfusion rate, when the error parameter is greater than a pre-defined value.

12. The prediction system (101) as claimed in claim 8, wherein the processor (113) represents the three-dimensional thermal image by one or more colors depending on the plurality of temperature values and the plurality of intermediate temperature values.

13. The prediction system (101) as claimed in claim 8, wherein the processor (113) generates the three-dimensional thermal image of the breast of the subject based on at least one of linear interpolation and quadratic interpolation techniques.

14. The prediction system (101) as claimed in claim 8, wherein the processor (113) classifies the breast tissue of the subject into corresponding category based on a relative score, wherein the relative score is generated based on a pre-defined data of healthy tissues and the plurality of temperature values associated with the subject.

15. A non-transitory computer readable medium including instruction stored thereon that when processed by at least one processor (113) cause a prediction system (101) to perform operation comprising:
receiving a plurality of temperature values associated with a breast of a subject from a device, wherein the device comprises a plurality of thermal sensors locatable on pre-determined positions of the breast of the subject, wherein each temperature value is represented by a node that corresponds to at least one pre-determined position of the breast of the subject;
estimating a plurality of intermediate temperature values within the plurality of temperature values, based on density value, thermal conductivity of the breast tissue, blood perfusion rate, specific heat capacity of the blood, arterial temperature, metabolic heat generation value in a normal and in an abnormal tissue, at least one of tetrahedral patterns and hexahedral patterns formed on a predefined model of the breast of the subject, and three dimensional coordinates on at least one of the tetrahedral patterns and the hexahedral patterns;
generating a three-dimensional thermal image of the breast of the subject based on the plurality of temperature values and the plurality of intermediate temperature values and an error parameter; and;

predicting depth of the abnormal tissue in the breast tissue of the subject based on, the three-dimensional thermal image, wherein the depth of the abnormal tissue is predicted by the three-dimensional coordinates of a temperature value associated with a higher temperature value among the plurality of temperature values and the plurality of intermediate temperature values.

16. The medium as claimed in claim 15, wherein the instruction causes the processor (113) to determine the plurality of intermediate temperature values using at least one of a Finite Element Method (FEM) and a Finite Volume Method (FVM) technique.

17. The medium as claimed in claimed 15, wherein the instruction causes the processor (113) to calculate the error parameter iteratively based on the plurality of temperature values received from the device and the plurality of intermediate temperature values.

18. The medium as claimed in claim 15, wherein the instruction causes the processor (113) to update the metabolic heat generation value in the abnormal tissue and the blood perfusion rate, when the error parameter is greater than a pre-defined value.

19. The medium as claimed in claim 15, wherein the three-dimensional thermal image is represented by one or more colors depending on the plurality of temperature values and the plurality of intermediate temperature values.

20. The medium as claimed in claim 15, wherein the instruction causes the processor (113) to generate the three-dimensional thermal image of the breast of the subject based on at least one of linear interpolation and quadratic interpolation techniques.

21. The medium as claimed in claim 15, wherein the instruction causes the processor (113) to classify the breast tissue of the subject into corresponding category based on a relative score, wherein the relative score is generated based on a pre-defined data of healthy tissues and the plurality of temperature values associated with the subject.

* * * * *

UNITED STATES PATENT AND TRADEMARK OFFICE
CERTIFICATE OF CORRECTION

PATENT NO. : 11,793,408 B2
APPLICATION NO. : 17/851810
DATED : October 24, 2023
INVENTOR(S) : Seema Ansari et al.

It is certified that error appears in the above-identified patent and that said Letters Patent is hereby corrected as shown below:

In the Specification

Column 11, Lines 36-37, delete "$Q_{nm}$" and insert -- $Q_{nm}+Q_{mm}$ --

Column 11, Lines 38-39, delete "where $Q_{nm}$=metabolic heat generation in normal tissue $Q_{mem}$ metabolic heat generation abnormal tissue." and insert --where $Q_{nm}$=metabolic heat generation in normal tissue and $Q_{mm}$ = metabolic heat generation in abnormal tissue.--

In the Claims

Column 20, Line 4, Claim 8, delete "and;" and insert --and--

Column 20, Line 17, Claim 10, delete "claimed 8" and insert --claim 8--

Column 20, Line 45, Claim 15, delete "cause" and insert --causes--

Column 20, Line 67, Claim 15, delete "and;" and insert --and--

Column 21, Line 13, Claim 17, delete "claimed 15" and insert --claim 15--

Signed and Sealed this
Thirteenth Day of February, 2024

Katherine Kelly Vidal
*Director of the United States Patent and Trademark Office*